US010429360B2

(12) United States Patent
Ohashi

(10) Patent No.: US 10,429,360 B2
(45) Date of Patent: Oct. 1, 2019

(54) LIQUID CHROMATOGRAPH CONTROL SYSTEM AND LIQUID CHROMATOGRAPH CONTROL METHOD

(71) Applicant: SHIMADZU CORPORATION, Kyoto-shi, Kyoto (JP)

(72) Inventor: Hiroshi Ohashi, Otsu (JP)

(73) Assignee: SHIMADZU CORPORATION, Kyoto-shi (JP)

(*) Notice: Subject to any disclaimer, the term of this patent is extended or adjusted under 35 U.S.C. 154(b) by 733 days.

(21) Appl. No.: 14/636,524

(22) Filed: Mar. 3, 2015

(65) Prior Publication Data

US 2015/0253295 A1 Sep. 10, 2015

(30) Foreign Application Priority Data

Mar. 4, 2014 (JP) ................................. 2014-041741

(51) Int. Cl.
*G01N 30/32* (2006.01)
*G01N 30/46* (2006.01)
(Continued)

(52) U.S. Cl.
CPC ........... *G01N 30/32* (2013.01); *G01N 30/468* (2013.01); *G01N 30/34* (2013.01); *G01N 30/466* (2013.01);
(Continued)

(58) Field of Classification Search
CPC .................................................. G01N 30/468
See application file for complete search history.

(56) References Cited

U.S. PATENT DOCUMENTS 3,831,555 A * 8/1974 Srinivas ................. G01N 30/56
 118/506
4,285,810 A * 8/1981 Kirkland ................... B03B 5/00
 73/865.5
(Continued)

FOREIGN PATENT DOCUMENTS

JP 2012-53063 A 3/2012
JP 2013-24603 A 2/2013

OTHER PUBLICATIONS

Office Action dated Oct. 10, 2017, issued in counterpart Japanese Application No. 2014-041741, with English translation. (9 pages).

*Primary Examiner* — Lisa M Caputo
*Assistant Examiner* — Alex T Devito
(74) *Attorney, Agent, or Firm* — Westerman, Hattori, Daniels & Adrian, LLP

(57) ABSTRACT

To reduce damage to a column caused during column switching when performing successive analyses while switching columns, provided is liquid chromatograph control system 70 for analyzing a sample according to a schedule table where analysis conditions and execution order of a plurality of analyses are described. Control system 70 includes: schedule reader 66 for reading out two consecutively executed analysis conditions; column comparator 67 for comparing columns used in the two analysis conditions; insertion method file creator for creating an insertion method file so that the flow rate of a mobile phase sent to the column used in later one of the two analyses is increased in stages toward a flow rate determined for the later analysis, where the columns are different between the two analysis conditions; and a schedule table creator 63 for inserting the insertion method file into immediately before the later analysis in the schedule table.

6 Claims, 5 Drawing Sheets

(51) Int. Cl.
*G01N 30/02* (2006.01)
*G01N 30/34* (2006.01)
*G01N 35/00* (2006.01)

(52) U.S. Cl.
CPC ... *G01N 35/0092* (2013.01); *G01N 2030/027* (2013.01); *G01N 2030/324* (2013.01)

(56) References Cited

U.S. PATENT DOCUMENTS

| | | | | |
|---|---|---|---|---|
| 4,416,783 A | * | 11/1983 | Noguchi | B01D 15/206 210/198.2 |
| 2005/0193262 A1 | * | 9/2005 | Osaka | G01N 35/00871 714/37 |
| 2013/0018598 A1 | * | 1/2013 | Ohashi | G01N 30/34 702/25 |

* cited by examiner

| ANALYSIS NO. | SAMPLE NAME | INJECTION AMOUNT | METHOD FILE NAME | DATA FILE NAME | ... |
|---|---|---|---|---|---|
| 1 | SAMPLE 1 | 10 | FILE 1 | DATA 1 | ... |
| 2 | SAMPLE 2 | 10 | FILE 2 | DATA 2 | ... |
| 3 | SAMPLE 3 | 10 | FILE 3 | DATA 3 | ... |
| ⋮ | ⋮ | ⋮ | ⋮ | ⋮ | |

LIQUID CHROMATOGRAPH CONTROL SYSTEM AND LIQUID CHROMATOGRAPH CONTROL METHOD

TECHNICAL FIELD

The present invention relates to a liquid chromatograph control system, and, more particularly, to a liquid chromatograph control system in which a plurality of columns are switchingly used, and a liquid chromatograph control method using the liquid chromatograph control system.

BACKGROUND ART

A liquid chromatograph is an analysis apparatus in which: a mobile phase (also called eluent) of a liquid and a sample injected into the mobile phase are pressurized by a pump or the like to be caused to pass through a column; and components in the sample are separated and detected based on a difference in interaction (such as adsorption, distribution, ion exchange, and size exclusion) between a stationary phase (also called filler) and the mobile phase in the column.

In the liquid chromatograph, a sample is analyzed under various conditions, in some cases, in order to find the best analysis conditions for the sample (hereinafter, this operation is called method scouting). In the method scouting, the kind of mobile phase, the kind of column, the flow rate of a pump, the temperature of a column oven for heating the column, and the like are set as parameters. Hence, the liquid chromatograph that performs the method scouting is capable of switching these parameters (see Patent Literature 1).

An example of the liquid chromatograph as described above is illustrated in FIG. 6. A liquid chromatograph 1 of FIG. 6 includes a liquid-sending section 10, an auto-sampler 20, a column oven 30, a detection section 40, a system controller 50 for controlling each of these sections, and a control system 60 for managing analysis operations through the system controller 50 and processing data obtained by the detection section 40. An operation section 71 including a keyboard and a mouse, and a display section 72 including a display unit are connected to the control system 60. A plurality of columns 32a to 32f are provided in the column oven 30, and the plurality of columns 32a to 32f are switched by passage-switching sections 31 and 33. In the liquid-sending section 10, solvent containers 11a to 11d and 12a to 12d in which various mobile phases are contained are respectively connected to liquid-sending pumps $P_A$ and $P_B$ through deaerators 13 and 14 and solvent-switching valves 15 and 16. Examples of the used mobile phases include: aqueous solvents such as water and aqueous solutions obtained by adding various salts to water; and organic solvents such as methanol, acetonitrile and hexane. An aqueous solvent drawn from one of the solvent containers 11a to 11d and an organic solvent drawn from one of the solvent containers 12a to 12d are mixed with each other by a gradient mixer 17 as needed, whereby a mobile phase having a predetermined composition is prepared.

The mobile phase having the predetermined composition that is prepared by the liquid-sending section 10 passes through the auto-sampler 20 to flow into one of the plurality of columns 32a to 32f in the column oven 30. Before that, a sample is injected into the mobile phase by the auto-sampler 20, and the sample passes through the column while being carried by the flow of the mobile phase. In the process, components in the sample are temporally separated and sequentially detected by the detection section 40 provided with a detector 41 such as a photodiode array (PDA) detector.

A number of analyses under various analysis conditions are controlled by the control system 60 embodied by a computer, and are automatically processed. The various analysis conditions are described in a file called "method file", which is managed by an analysis condition setter 62 in the control system 60, and is stored in a memory 61 in the control system 60. A schedule table creator 63 in the control system 60 creates a file of data called a "schedule table" which is a table describing which analysis conditions are executed in which order. In the schedule table, a sample to be analyzed and an analysis condition for the sample are described in a row, and a series of rows are listed in the columnar direction as analysis time series. A method file is cited as the analysis condition. According to the schedule table, an analysis controller 64 in the control system 60 controls each section in the liquid chromatograph 1 such that a series of analyses are executed under the analysis conditions at predetermined timing. A data processor 65 in the control system 60 acquires an analysis result under each analysis condition and performs processes such as chromatogram creation.

CITATION LIST

Patent Literature

[Patent Literature 1] JP 2013-024603 A

SUMMARY OF INVENTION

Technical Problem

Conventionally, in method scouting in which a sample is analyzed under a plurality of analysis conditions according to a schedule table in which the analysis order is described, in the case where a column is changed to another (when a column switching is made) in successive analyses, a mobile phase is sent to a column used in the next analysis at a target flow rate determined for the next analysis, from immediately after the column switching. Hence, in the case where the target flow rate is high, the column used after the column switching may be damaged by the sudden flow of the mobile phase into the column at the target flow rate.

The present invention, which has been made in view of the above, has an object to reduce damage to a column caused at the time of column switching in the case of performing successive analyses while switching columns.

Solution to Problem

A liquid chromatograph control method according to the present invention, which has been made in order to achieve the above-mentioned object, is a liquid chromatograph control method in which a sample is analyzed using a liquid chromatograph provided with a function of switching columns, according to a schedule table in which analysis conditions and execution order of a plurality of analyses are described, the control method including the steps of: a) reading out two analysis conditions consecutively executed in the schedule table; b) comparing columns used in the two read-out analysis conditions; c) creating an insertion method file to the effect that a flow rate of a mobile phase sent to the column used in later one of the two analyses is increased in stages from a flow rate lower than a target flow rate determined for the later analysis toward the target flow rate, in a case where the compared columns are different from each other; and d) inserting the insertion method file into immediately before the later analysis in the schedule table.

A liquid chromatograph control system according to the present invention, which has been made in order to achieve the above-mentioned object, is a liquid chromatograph control system that is provided with a function of switching columns and analyzes a sample according to a schedule table in which analysis conditions and execution order of a plurality of analyses are described, the control system including: a) a schedule reader for reading out two analysis conditions consecutively executed in the schedule table; b) a column comparator for comparing columns used in the two analysis conditions read out by the schedule reader; c) an insertion method file creator for creating an insertion method file to the effect that a flow rate of a mobile phase sent to the column used in later one of the two analyses is increased in stages from a flow rate lower than a target flow rate determined for the later analysis toward the target flow rate, in a case where the columns are different between the two analysis conditions; and d) a schedule table creator for inserting the insertion method file into immediately before the later analysis in the schedule table.

Sending time of the mobile phase in each stage (that is, each flow rate) when the flow rate of the mobile phase is increased in stages as described above is designated in advance by, for example, a user. Alternatively, the pressure at the entrance of the column used in the later analysis is monitored during mobile phase sending according to the insertion method file, and, after the flow rate of the mobile phase is increased one stage, the flow rate of the mobile phase may be increased to the next stage when an increasing speed of the pressure becomes equal to or less than a predetermined threshold (or when the pressure increase ends).

Advantageous Effects of Invention

In the liquid chromatograph control system and the liquid chromatograph control method configured as described above according to the present invention, in the case where the used columns are different between the two analyses consecutively executed in the schedule table, the flow rate of the mobile phase sent to the column used in the later analysis is controlled so as to be increased in stages toward the target flow rate. This allows the mobile phase to gently flow into the column used in the later analysis, and hence damage to the column can be reduced.

DESCRIPTION OF EMBODIMENTS

Hereinafter, modes for carrying out the present invention are described by way of embodiments.

Embodiment 1

Figure 1:
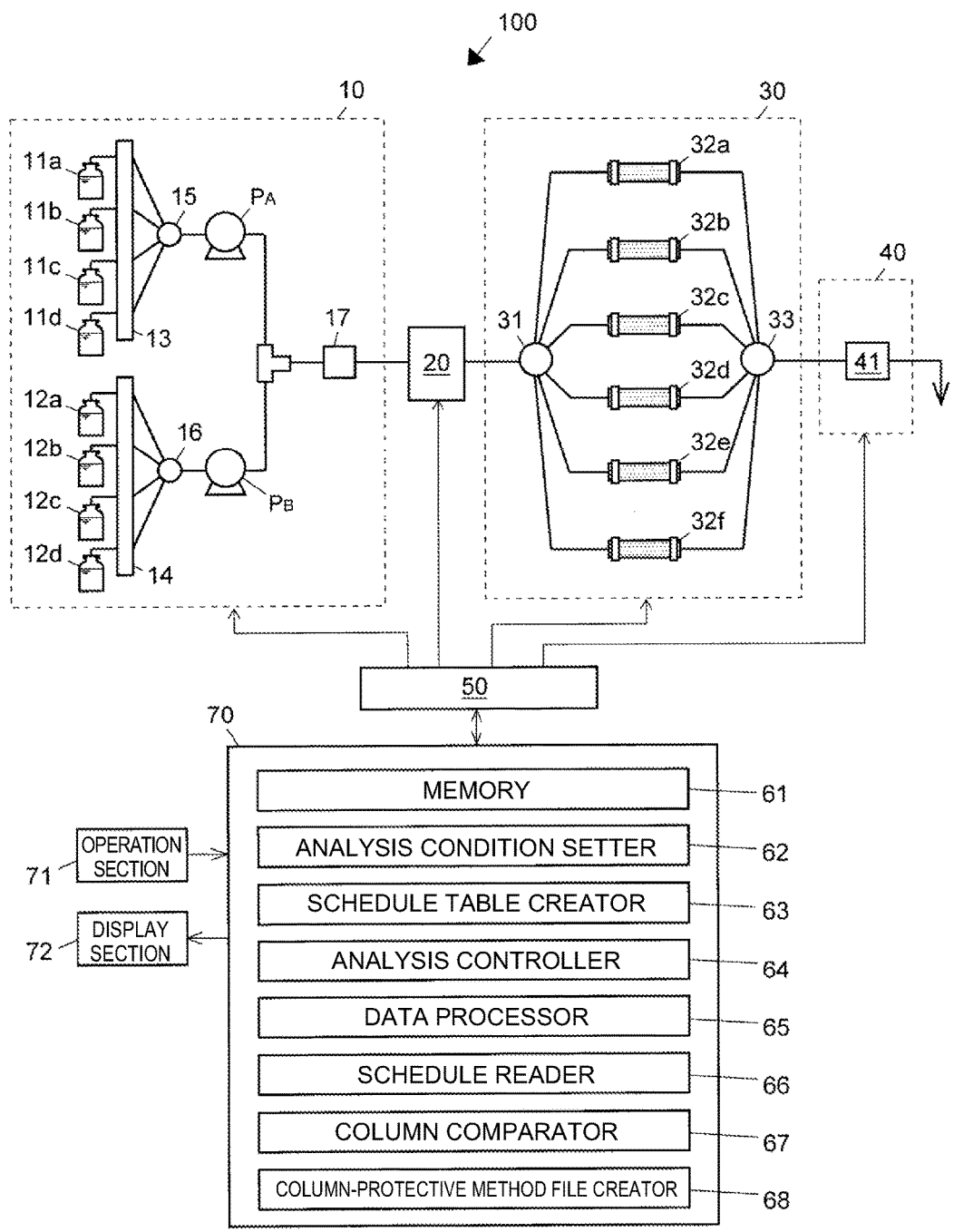
FIG. 1 is a diagram describing a liquid chromatograph according to an embodiment of the present invention.
Figure 2:
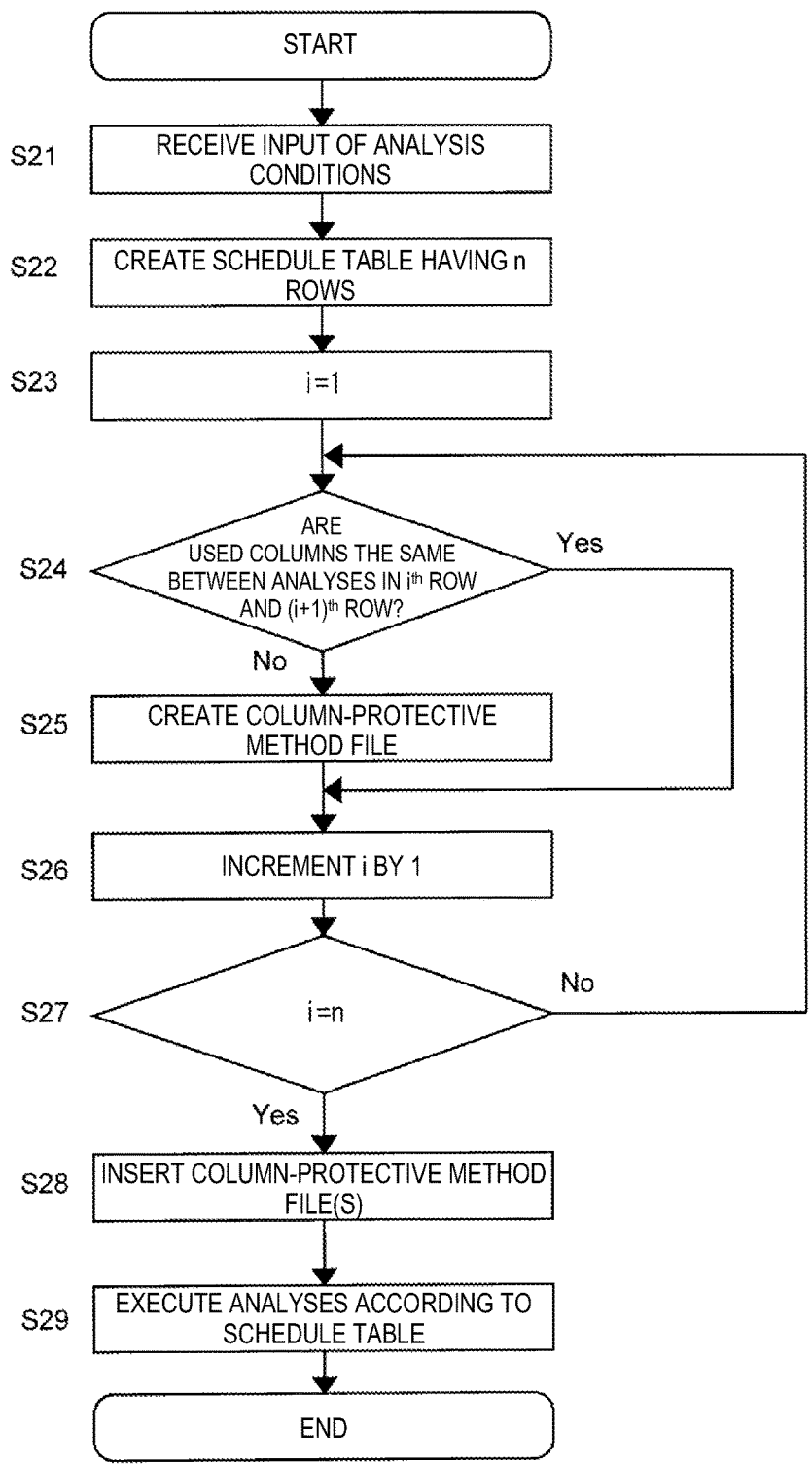
FIG. 2 is a flowchart describing the analysis order of the liquid chromatograph according to the embodiment.
Figure 6:
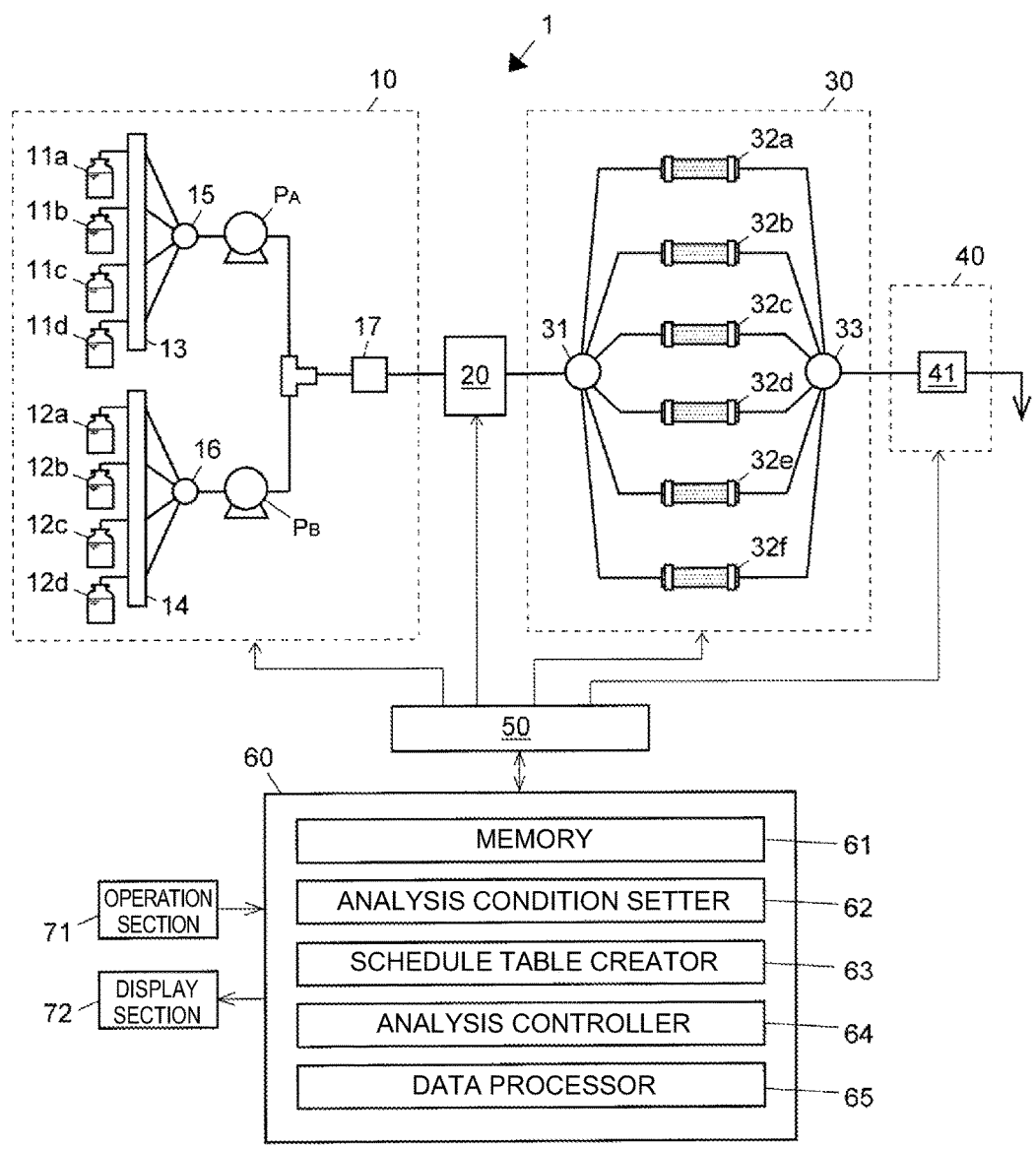
FIG. 6 is a diagram describing a conventional liquid chromatograph.

FIG. 1 is a schematic configuration diagram of a liquid chromatograph according to an embodiment of the present invention, and FIG. 2 is a flowchart describing the analysis order of the liquid chromatograph. The same constituent elements as those in FIG. 6 are denoted by the same reference signs, and description thereof is omitted as appropriate.

A liquid chromatograph 100 of the present embodiment includes a liquid-sending section 10, an auto-sampler 20, a column oven 30, a detection section 40, a system controller 50, and a control system 70. An operation section 71 including a keyboard and a mouse and a display section 72 including a display unit are connected to the control system 70. The control system 70 includes a memory 61, an analysis condition setter 62, a schedule table creator 63, an analysis controller 64, and a data processor 65, similarly to the control system 60 of the conventional liquid chromatograph 1. In addition, the control system 70 includes a schedule reader 66, a column comparator 67, and a column-protective method file creator 68. The column-protective method file creator 68 corresponds to an insertion method file creator of the present invention. The control system 70 corresponds to a liquid chromatograph control system of the present invention and is embodied by a computer.

In executing method scouting, first, the schedule table creator 63 displays a predetermined setting screen (not illustrated) on the display section 72, and receives an input by a user through the operation section 71 (Step S21). The user inputs, for each of a plurality of analyses executed in the method scouting, the name of a sample to be analyzed and the injection amount of the sample as well as a method file name used in the analysis and a data file name used to save an analysis result.

Figures 3, 4:
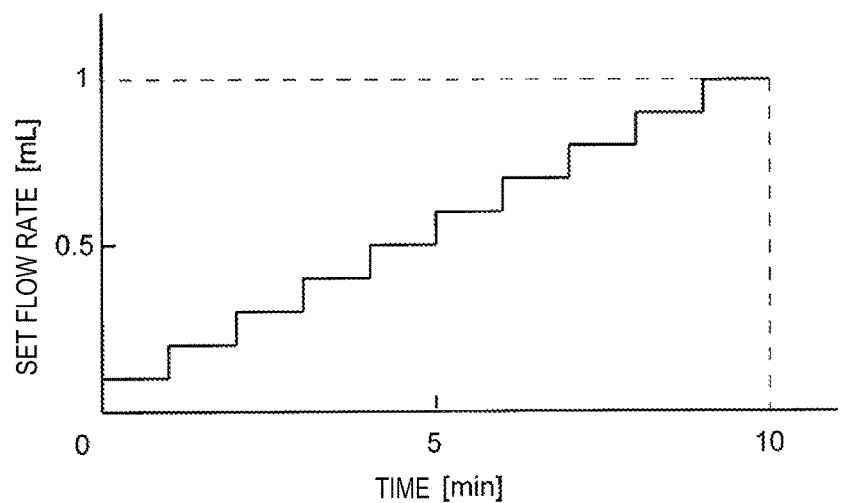
FIG. 3 is a diagram illustrating a schedule table created in the embodiment.
FIG. 4 is a diagram describing a mobile phase profile of a column-protective method file created in the embodiment.

The schedule table creator 63 creates a schedule table in which the execution order of the plurality of analyses is described, based on the input by the user in Step S21, and stores the schedule table in the memory 61 (Step S22). As a result, for example, such a schedule table as illustrated in FIG. 3 is created. In the case where the number of the plurality of analyses is n (n: an integer equal to or more than 2), a schedule table having n rows is created.

After the creation of the schedule table, the schedule reader 66 first initializes a variable i corresponding to the number of rows in the schedule table to 1 (Step S23), and then reads out analysis conditions in the $i^{th}$ row and the $(i+1)^{th}$ row from the memory 61. Information on a column used in analysis is not directly described in the schedule table, and is described in a method file cited by the schedule table. Hence, the schedule reader 66 accesses each method file to read out the information on the column used in analysis. The column comparator 67 compares the analysis conditions in the $i^{th}$ row and the $(i+1)^{th}$ row to determine whether or not the used columns are the same between the two rows (Step S24).

In the case where the used columns are the same between the analyses in the $i^{th}$ row and the $(i+1)^{th}$ row and where column switching is not required between the two analyses, for example, in the case where a difference between the analysis conditions in the $i^{th}$ row and the $(i+1)^{th}$ row is only a change in temperature of the column oven 30, the processing immediately goes to Step S26 to be described later, and the variable i is incremented by 1.

Meanwhile, in the case where the used columns are different between the analyses in the $i^{th}$ row and the $(i+1)^{th}$ row and where column switching is required between the two analyses, the column-protective method file creator 68 creates an insertion method file (hereinafter, this file is called "column-protective method file") to the effect that the same mobile phase as that in later one of the two analyses is sent to a column (hereinafter, this column is called "selected column") used in the later analysis, while the flow rate of the mobile phase is increased in stages up to a predetermined flow rate (Step S25). For example, it is assumed in the schedule table illustrated in FIG. 3 that: a column 32a is described as the column used in analysis in "File 1" and "File 2" that are method files respectively cited in analysis Nos. 1 and 2; a column 32b is described as the column used in analysis in "File 3" that is a method file cited in analysis No. 3; and the flow rate (target flow rate) of the mobile phase is 1 mL. In this case, at the time of switching from the analysis of analysis No. 2 to the analysis of analysis No. 3, switching of the columns used in analysis (the column 32a→the column 32b) is required. Hence, the column-protective method file creator 68 creates a column-protective method file to the effect that the flow rate of the mobile phase is increased in stages toward the predetermined flow rate in units of flow rate that does not cause damage to the column 32b (hereinafter, the flow rate of the mobile phase increased in one stage is called "unit flow rate"). Here, description is given of an example in which the flow rate (target flow rate) of the mobile phase described in the method file used in the analysis in the $(i+1)^{th}$ row in the schedule table is defined as the predetermined flow rate, but the predetermined flow rate is not limited thereto. For example, the flow rate one stage before the target flow rate is reached may be defined as the predetermined flow rate.

In the present embodiment, in Step S21, the user inputs in advance the number of stages required up to the predetermined flow rate and the time required for each stage. After that, in Step S25, the column-protective method file creator 68 calculates the unit flow rate from the predetermined flow rate and the number of stages. For example, if the user inputs 10 as the number of stages and 1 minute as the time required for each stage, the column-protective method file is created as a file including an instruction to the effect that the flow rate of the mobile phase is increased for a total of 10 minutes in 10 stages with a unit flow rate of 0.1 mL up to a predetermined flow rate of 1 mL, as a mobile phase profile illustrated in FIG. 4.

The memory 61 stores the column-protective method file created by the column-protective method file creator 68, and also stores information on an insertion destination (a registration destination) of the column-protective method file (that is, between the $i^{th}$ row and the $(i+1)^{th}$ row in the schedule table where the column-protective method file is inserted).

Subsequently, the schedule reader 66 increments the variable i by 1 (Step S26), and compares i with n (Step S27). If i is not equal to n, every analysis condition comparison between rows adjacent to each other in the schedule table having the n rows is not performed. Hence, the processing returns to Step S24, and the above-mentioned steps are repeated. If i is equal to n, the comparison between two consecutively executed analysis conditions is ended.

After the end of the comparison between consecutively executed analysis conditions, the schedule table creator 63 reads out, from the memory 61, one or more column-protective method files created as described above and the information on the insertion destinations (the registration destinations) of the column-protective method files, and inserts to register a new row for citing each of the column-protective method files into between a row and a row in the schedule table, which is designated as the insertion destination (the registration destination) (Step S28).

Subsequently, the analysis controller 64 executes analyses according to the schedule table updated as described above (Step S29). If all the analyses described in the schedule table are executed, a series of analyses is ended. In the case where all the columns used in the analysis conditions described in the schedule table having the n rows are the same, no column-protective method file is created, and the schedule table is not updated. Hence, the analysis controller 64 executes analyses according to the original schedule table having the n rows.

As described above, according to the liquid chromatograph 100 of the present embodiment, in the case where used columns are different between two consecutively executed analyses, the column-protective method file creator 68 creates a column-protective method file to the effect that the flow rate of the mobile phase sent to the column used in later one of the two analyses is increased in stages up to a predetermined flow rate, and the schedule table creator 63 inserts to register the column-protective method file into immediately before the later analysis in the schedule table. Then, in performing analyses according to the schedule table, the analysis controller 64 increases the flow rate of the mobile phase sent to the selected column in stages with a unit flow rate, according to the column-protective method file. This allows the mobile phase to gently flow into the selected column, and hence damage to the column can be reduced. As a result, the life of the column can be lengthened, and costs used for the system can be suppressed.

Embodiment 2

Another embodiment of the liquid chromatograph according to the present invention is described with reference to FIG. 5. The same constituent elements as those in FIG. 1 are denoted by the same reference signs, and description thereof is omitted as appropriate.

Figure 5:
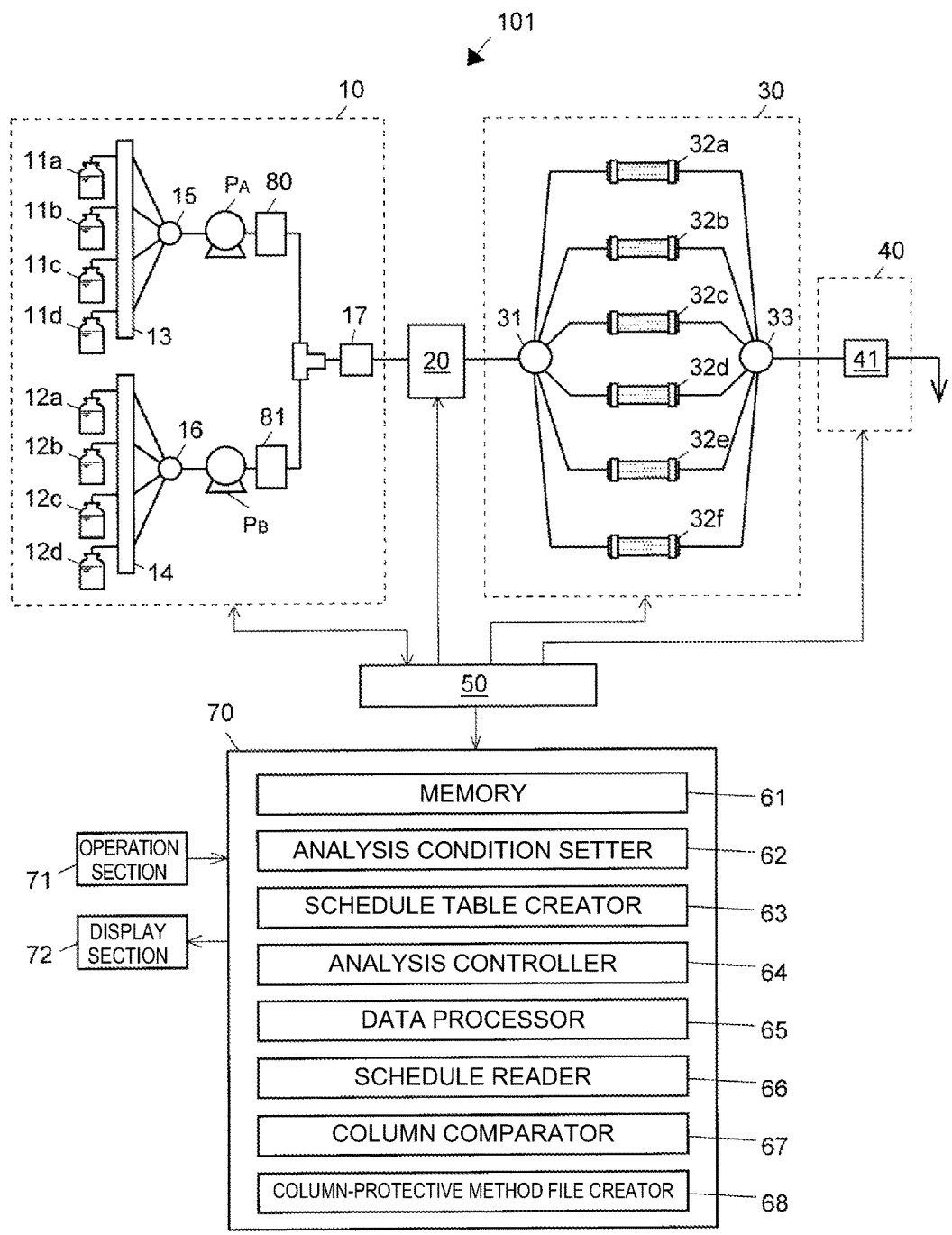
FIG. 5 is a diagram describing a liquid chromatograph according to another embodiment of the present invention.

A liquid chromatograph 101 illustrated in FIG. 5 includes a pressure sensor 80 and a pressure sensor 81 for detecting the pressure at the entrance of each column, in addition to the configuration of the liquid chromatograph 100 illustrated in FIG. 1. In the present embodiment, description is given of an example in which these pressure sensors are respectively provided to the exits of liquid-sending pumps $P_A$ and $P_B$, but the pressure sensors may be provided to any points within passages from the liquid-sending pumps $P_A$ and $P_B$ to the entrances of the plurality of columns 32a to 32f.

In Embodiment 1, description is given of an example in which liquid-sending time in each stage when the flow rate of the mobile phase sent to the selected column is increased in stages with a unit flow rate is determined in advance before analysis start. In comparison, in the liquid chromatograph 101 according to the present embodiment, the pressure at the entrance of the selected column is measured during liquid sending according to the column-protective method file, and the liquid-sending time in each stage is determined each time based on the measurement value.

In the present embodiment, information on pressures detected by the pressure sensor 80 and the pressure sensor 81 is sent to the control system 70. As the flow rate of the mobile phase sent to a column is increased, the pressure at the entrance of the column becomes higher accordingly. After that, when the flow rate of the mobile phase flowing in the column becomes constant, the pressure at the entrance of the column gradually becomes stable to exhibit a constant value. In view of this, in the present embodiment, during liquid sending according to the column-protective method file, after the flow rate of the mobile phase is increased one stage, the flow rate of the mobile phase is increased to the next stage when the increasing speed of the pressure at the entrance of the selected column becomes equal to or less than a predetermined threshold (or when the pressure increase at the entrance of the selected column ends).

In this way, the pressure at the entrance of the selected column is actually measured. After the flow rate of the mobile phase is increased one stage, stabilization of the pressure is awaited each time, and then the flow rate of the mobile phase is increased to the next stage. This configuration can more reliably reduce damage to the column.

REFERENCE SIGNS LIST 1, 100, 101 . . . Liquid Chromatograph
10 . . . Liquid-Sending Section
11a to 11d, 12a to 12d . . . Solvent Container
13, 14 . . . Deaerator
15, 16 . . . Solvent-Switching Valve
17 . . . Gradient Mixer
20 . . . Auto-Sampler
30 . . . Column Oven
31, 33 . . . Passage-Switching Section
32a to 32f . . . Column
40 . . . Detection Section
41 . . . Detector
50 . . . System Controller
60, 70 . . . Control System
61 . . . Memory
62 . . . Analysis Condition Setter
63 . . . Schedule Table Creator
64 . . . Analysis Controller
65 . . . Data Processor
66 . . . Schedule Reader
67 . . . Column Comparator
68 . . . Column-Protective Method File Creator
71 . . . Operation Section
72 . . . Display Section
80, 81 . . . Pressure Sensor

The invention claimed is:

1. A liquid chromatograph control method in which a sample is analyzed using a liquid chromatograph provided with a function of switching columns, according to a schedule table in which analysis conditions and execution order of a plurality of analyses are described, the control method comprising the steps of:
 a) reading out two analysis conditions consecutively executed in the schedule table;
 b) comparing columns used in the two read-out analysis conditions;
 c) creating an insertion method file to the effect that a flow rate of a mobile phase sent to the column used in later one of the two analyses is increased in stages from a flow rate lower than a target flow rate determined for the later analysis toward the target flow rate, in a case where the compared columns are different from each other; and
 d) inserting the insertion method file into immediately before the later analysis in the schedule table.

2. The liquid chromatograph control method according to claim 1, wherein sending time of the mobile phase in each stage when the flow rate of the mobile phase is increased in stages is designated in advance by a user.

3. The liquid chromatograph control method according to claim 1, wherein
 a pressure at an entrance of the column used in the later analysis is monitored during mobile phase sending according to the insertion method file, and
 after the flow rate of the mobile phase is increased one stage, the flow rate of the mobile phase is increased to the next stage when an increasing speed of the pressure becomes equal to or less than a predetermined threshold.

4. A liquid chromatograph control system that is provided with a function of switching columns and analyzes a sample according to a schedule table in which analysis conditions and execution order of a plurality of analyses are described, the control system comprising:
 a) a schedule reader for reading out two analysis conditions consecutively executed in the schedule table;
 b) a column comparator for comparing columns used in the two analysis conditions read out by the schedule reader;
 c) an insertion method file creator for creating an insertion method file to the effect that a flow rate of a mobile phase sent to the column used in later one of the two analyses is increased in stages from a flow rate lower than a target flow rate determined for the later analysis toward the target flow rate, in a case where the columns are different between the two analysis conditions; and
 d) a schedule table creator for inserting the insertion method file into immediately before the later analysis in the schedule table.

5. The liquid chromatograph control system according to claim 4, wherein sending time of the mobile phase in each stage when the flow rate of the mobile phase is increased in stages is designated in advance by a user.

6. The liquid chromatograph control system according to claim 4, wherein
 a pressure at an entrance of the column used in the later analysis is monitored during mobile phase sending according to the insertion method file, and
 after the flow rate of the mobile phase is increased one stage, the flow rate of the mobile phase is increased to the next stage when an increasing speed of the pressure becomes equal to or less than a predetermined threshold.

* * * * *